(12) United States Patent
Soto (10) Patent No.: US 8,316,625 B2
(45) Date of Patent: Nov. 27, 2012

(54) ENHANCEMENTS TO A SUBSTANTIALLY CLOSED SYSTEM FOR SAFELY DISPOSING HAZARDOUS MATERIAL

(75) Inventor: Louis M. Soto, Miramar, FL (US)

(73) Assignee: Louis M. Soto, Miramar, FL (US)

( * ) Notice: Subject to any disclaimer, the term of this patent is extended or adjusted under 35 U.S.C. 154(b) by 279 days.

(21) Appl. No.: 12/788,002

(22) Filed: May 26, 2010

(65) Prior Publication Data

US 2010/0234665 A1 Sep. 16, 2010

Related U.S. Application Data

(63) Continuation-in-part of application No. 11/946,283, filed on Nov. 28, 2007, now Pat. No. 7,854,107.

(51) Int. Cl.
*B65B 31/02* (2006.01)
*B65B 25/00* (2006.01)

(52) U.S. Cl. .......... 53/493; 53/502; 53/77; 53/510; 312/1; 588/900

(58) Field of Classification Search ............ 53/396, 53/432, 434, 469, 493, 502, 77, 507, 510, 53/512, 284.7; 110/235, 242, 346; 312/1; 422/4, 24; 588/249.5, 260, 900; *B65B 25/00, B65B 29/00, 31/02*
See application file for complete search history.

(56) References Cited

U.S. PATENT DOCUMENTS

| | | | | |
|---|---|---|---|---|
| 3,511,022 A | * | 5/1970 | Finley et al. | 53/512 |
| 3,596,429 A | * | 8/1971 | Vogt | 53/284.7 |
| 3,939,998 A | * | 2/1976 | Soltermann | 53/502 |
| 4,297,827 A | * | 11/1981 | Allison | 53/282 |
| 4,592,192 A | * | 6/1986 | Jacob et al. | 53/512 |
| 4,688,371 A | * | 8/1987 | Hecht | 53/502 |

(Continued)

FOREIGN PATENT DOCUMENTS

FR 2758540 A1 * 7/1998

(Continued)

OTHER PUBLICATIONS

"Preventing Occupational Exposure to Antineoplastics and Other Hazardous Drugs in Workplace Settings," NIOSH, Pub. No. 2004-165, Sep. 2004, 48 pages.

(Continued)

*Primary Examiner* — Stephen F Gerrity
(74) *Attorney, Agent, or Firm* — Patents on Demand P.A.; Brian K. Buchheit; Scott M. Garrett (57) ABSTRACT

A disposal unit can include a substantially air tight chamber, an insertion component, an air tight region of the air tight chamber containing a disposal container, an air holding region, an air extraction unit, an air sanitation component, a container sealant mechanism, and/or combinations thereof. The air holding region can be distinct from the air tight region and the remaining region of the substantially air tight chamber. The air extraction unit can be configured to capture air from the remaining region and place the captured air in the air holding region. Air can be optionally redirected from the air holding region into an airtight disposal container, which is thereafter sealed. The air sanitation component can be configured to sanitize the captured air to a predetermined air quality level. Harmful byproducts of the waste (e.g., toxic vapors) inserted in the disposal unit can be reduced and/or neutralized through sanitation and/or containment.

8 Claims, 4 Drawing Sheets

U.S. PATENT DOCUMENTS

| | | | |
|---|---|---|---|
| 4,991,633 A * | 2/1991 | Wong | 53/512 |
| 5,005,496 A | 4/1991 | Nagata | |
| 5,054,696 A | 10/1991 | Mennel | |
| 5,178,828 A * | 1/1993 | Uesugi | 422/22 |
| 5,425,316 A * | 6/1995 | Malone | 110/346 |
| 5,511,594 A * | 4/1996 | Brennan et al. | 141/98 |
| 5,528,880 A * | 6/1996 | Landolt | 53/432 |
| 5,715,646 A * | 2/1998 | Smekens | 53/502 |
| 5,791,123 A * | 8/1998 | Bolz | 53/434 |
| 5,810,060 A * | 9/1998 | Bolz et al. | 141/97 |
| 5,881,535 A * | 3/1999 | Gliniecki et al. | 53/469 |
| 5,890,781 A * | 4/1999 | Ryder | 312/1 |
| 5,972,291 A * | 10/1999 | Healy et al. | 588/900 |
| 6,367,518 B2 | 4/2002 | Duncan | |
| 6,428,122 B1 * | 8/2002 | Henry et al. | 312/1 |
| 6,742,703 B2 | 6/2004 | Esakov et al. | |
| 6,997,313 B2 | 2/2006 | Rigling | |
| 7,017,306 B2 | 3/2006 | Ryder | |
| 7,114,629 B2 | 10/2006 | Panek, Jr. | |
| 7,174,602 B1 | 2/2007 | Foral | |
| 2001/0004182 A1 * | 6/2001 | Bennison | 312/1 |
| 2003/0038564 A1 | 2/2003 | Drinkwater | |
| 2005/0004537 A1 * | 1/2005 | Dunn et al. | 604/322 |
| 2006/0119232 A1 | 6/2006 | Tattershall | |
| 2009/0149689 A1 * | 6/2009 | Crawford et al. | 588/3 |
| 2009/0280027 A1 * | 11/2009 | Hayman, Jr. | 422/4 |

FOREIGN PATENT DOCUMENTS

| | | | |
|---|---|---|---|
| JP | 52144600 A | * | 12/1977 |
| JP | 03275422 A | * | 12/1991 |
| WO | WO 2004110867 A1 | * | 12/2004 |

OTHER PUBLICATIONS

Spivey, S.M., et al., "Determining Sources of Workplace Contamination with Antineoplastic Drugs and Comparing Conventional IV Preparation With a Closed System," Hospital Pharmacy, 38(2):135-139, dated 2003, 1 page.

"ASHP Guidelines on Handling Hazardous Drugs," Am. J. Health-System Pharm., 2006-63, 1172-93, 20 pages, numbered 34-53.

Connor, T., "NIOSH Study of Health Care Workers in Three Sites-:Study Design and Results," 44th ASHP Midyear Clinical Meeting & Exhibition, Dec. 6-10, 2009, 48 pages.

* cited by examiner

ENHANCEMENTS TO A SUBSTANTIALLY CLOSED SYSTEM FOR SAFELY DISPOSING HAZARDOUS MATERIAL

CROSS-REFERENCE TO RELATED APPLICATIONS

This application is a continuation-in-part of U.S. patent application Ser. No. 11/946,283, filed 28 Nov. 2007, now U.S. Pat. No. 7,854,107. The entire contents of U.S. application Ser. No. 11/946,283 are incorporated by reference herein.

BACKGROUND

1. Field of the Invention

The present invention relates to the field waste disposal and, more particularly, to enhancements to a substantially closed system for disposing hazardous material, which can include harmful airborne substances (including vapors).

2. Description of the Related Art

The majority of trash receptacles include a lid, which is able to be opened, permitting waste to be placed inside. An interior bag of the trash receptacle is often able to be "tied" or otherwise manually sealed. Many types of refuse, however, can pose exposure hazards, which current trash disposal technologies fail to address. The hazards can result from airborne substances (which include vapors and air medium) being emitted from waste during the disposal process.

This can be true, for example, in a medical context, where bed sheets, gowns, linens, drinking cups, and other material are disposed of, each of which can contain traces of blood, sweat, and other body fluids, which can be hazardous to others. For instance, chemotherapy patients are occasionally irradiated, which results in their fluids containing traces of radioactivity to which waste disposal personnel at hospitals are constantly exposed. Additionally, airborne pathogens can be especially problematic for waste disposal employees at hospitals, who have a much higher than normal rate of health problems caused by constant exposure to hazardous material.

Other contexts where waste disposal practices are currently insufficient and/or dangerous include research lab waste disposal situations, toxic spill situations, generic hazmat situations, biological/chemical attacks in a terrorism/military situation, outbreak and epidemic situations, flooding and other national emergencies where mold, fungus, bacteria, viruses, and other potentially harmful substances are to be expected.

Public concern over the proper treatment and disposal of chemical waste products has increased over the past several years. This increase is due in part to an increased public awareness of dangerous chemicals being exposed to the environment that can have deleterious effects when improperly disposed of from within hospitals, out-patient clinics, and physicians' offices. Despite this increased awareness within limited contexts, few effective measures are being taken to resolve underlying problems. For example, hospitals currently have established awareness programs designed to teach its personnel to handle potentially harmful materials with care. These programs are designed to appease public pressure, but not to address the fundamental problem that current waste disposal techniques pose a health risk regardless of a level of care taken. What is needed is a new type of waste disposal receptacle, which minimizes (or eliminates) human contact with toxic wastes, which includes protection from airborne vapors.

SUMMARY OF THE INVENTION

The disclosure provides enhancements to a disposal unit for safely disposing hazardous materials in accordance with an embodiment of the inventive arrangements disclosed herein. The disposal unit can be configured to include one or more data measurement devices that can electronically capture waste data and convey the waste data to a central storage location. In another enhancement, the disposal unit can be configured to include one or more air sanitation mechanisms to treat potentially harmful airborne byproducts. One or more automatic sealant mechanism(s) can be used to enhance the disposal unit. Further, the configuration of the insertion tube through which the disposal unit receives waste can be varied utilizing multiple concentric tubes as well as spacers between the tubes.

The present invention can be implemented in accordance with numerous aspects consistent with the materials presented herein. One aspect of the present invention can include a waste disposal unit. The waste disposal unit can include a substantially air tight chamber, an insertion component for inserting waste into the chamber, an air tight (or substantially air tight) region of the air tight chamber containing a disposal container, an air holding region, an air extraction unit, an air sanitation component, and a container sealant mechanism (e.g., glue, adhesive, heat seal, other sealant). The air holding region can be distinct from the air tight region and the remaining region of the approximately air tight chamber. The air extraction unit can be configured to capture air from the remaining region and place the captured air in the air holding region. The air sanitation component can be configured to sanitize the captured air to a predetermined air quality level. The harmful airborne byproducts of the inserted waste can be reduced and/or neutralized. The container sealant mechanism can be configured to seal the disposal container.

Another aspect of the present invention can include a system that collects data regarding waste processed by the disposal unit. Such a system can include a disposal unit, a data collection component, and a data server. The disposal unit can include an approximately air tight chamber, an insertion component for inserting waste into the chamber, an air tight region of the approximately air tight chamber containing a disposal container, an air holding region distinct from the air tight region and a remaining region of the approximately air tight chamber, an air extraction unit, a container sealant mechanism, and one or more data measurement devices. The air extraction unit can be configured to capture air from the remaining region and to place the captured air in the air holding region. The container sealant mechanism can be configured to seal the disposal unit (e.g., a bag, container, etc.). The data measurement devices can be configured to determine waste data corresponding to a measurement of a property of the disposal unit and/or the inserted waste. The data collection component can be configured to receive the waste data from the disposal unit. The data server can include a data store and can be configured to receive and centrally store the collected waste data from the data collection component in a standardized format.

Still another aspect of the present invention can include a method for disposing waste. Disposal can begin with the receipt of waste through an aperture of an insertion component of a disposal unit. The disposal unit can be a substantially closed environment separate from an external operating environment of the disposal unit. The received waste can be placed into an air-tight disposal container. The aperture of the disposal unit can be sealed to isolate the substantially closed environment from the external operating environment. Air from within the substantially closed environment can be captured and placed within a holding unit. One or more handling processes can be executed (in series and/or simultaneous fashion) upon the captured air in the holding unit. The airtight disposal container containing the received waste can then be sealed. The disposal unit can thereafter be opened to discard the sealed air-tight disposal container.

It should be noted that various aspects of the invention can be implemented as a program for controlling computing equipment to implement the functions described herein, or as a program for enabling computing equipment to perform processes corresponding to the steps disclosed herein. This program may be provided by storing the program in a magnetic disk, an optical disk, a semiconductor memory or any other recording medium. The program can also be provided as a digitally encoded signal conveyed via a carrier wave. The described program can be a single program or can be implemented as multiple subprograms, each of which interact within a single computing device or interact in a distributed fashion across a network space.

BRIEF DESCRIPTION OF THE DRAWINGS

There are shown in the drawings, embodiments which are presently preferred, it being understood, however, that the invention is not limited to the precise arrangements and instrumentalities shown.

DETAILED DESCRIPTION OF THE INVENTION

Figure 1:
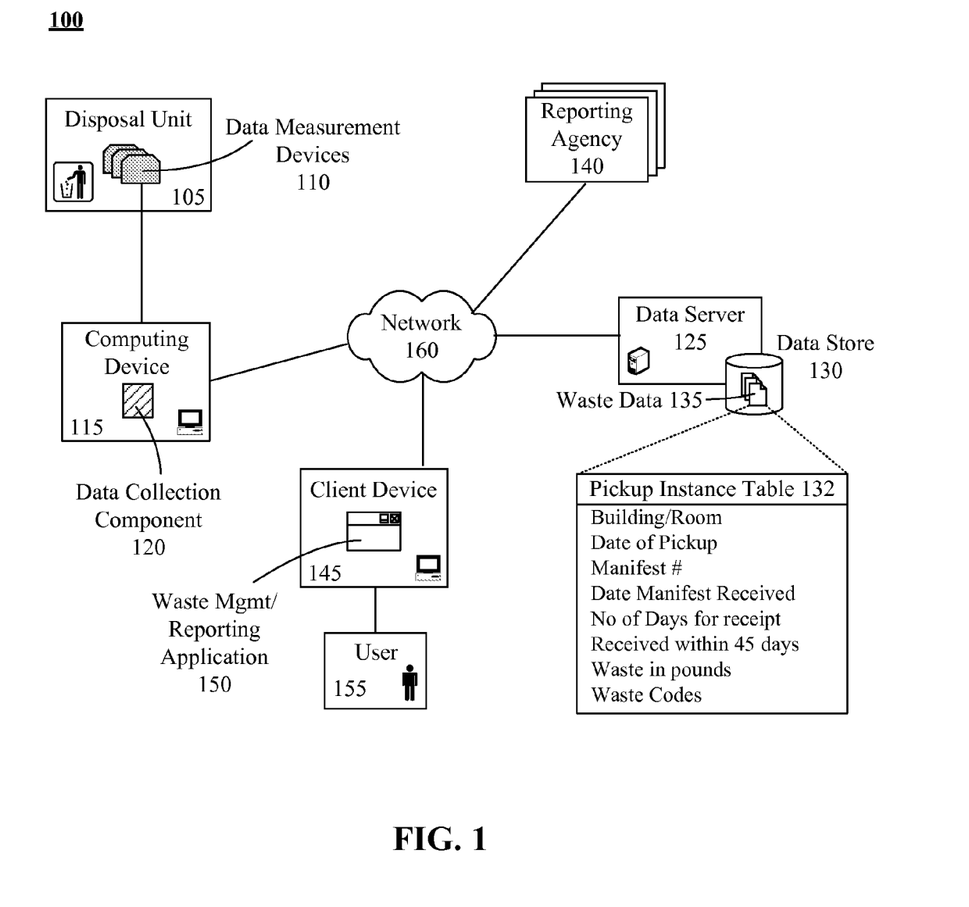
FIG. 1 is a schematic diagram of a waste disposal system that collects waste data regarding hazardous wastes processed by a disposal unit in accordance with an embodiment of the inventive arrangements disclosed herein.

FIG. 1 is a schematic diagram of a waste disposal system 100 that collects waste data 135 regarding the hazardous wastes processed by a disposal unit 105 in accordance with an embodiment of the inventive arrangements disclosed herein. In system 100, data measurements devices 110 installed within the disposal unit 105 can automatically collect one or more elements of waste data 135 that can be conveyed over a network 160 to a data server 125 for storage.

The disposal unit 105 can represent one of the many possible configurations described within U.S. patent application Ser. No. 11/946,283, which is to be considered as having been incorporated herein in its entirety.

For instance, and in one embodiment, the disposal unit 105 can be a disposal unit for a compounding aseptic containment isolator to prevent vapors and other wastes and/or waste byproducts from escaping. In another example, the disposal unit 105 can be coupled to a class II or type 2B biological safety cabinet. The disposal unit 105 is not limited to these configurations, which are provided for illustrative purposes only.

The disposal unit 105 can be designed to conform to state and/or federal regulation related to waste disposal and handling, especially hazardous wastes. For example, the disposal unit 105 and processes detailed herein can conform to the Resource Conservation and Recovery Act (RCRA) or 40 CFR Section 260. Thus, disposal unit 105 can be suited handling wastes falling under any of the four hazardous waste lists established by Environmental Protection Agency (EPA) regulations. This includes F-lists (non-specific source wastes), K-list (source-specific wastes), P-list, and U-list (discarded commercial chemical products). In one embodiment, special emphasis can be placed on using disposal unit to handle discarded chemical products (currently defined by 40 CFR Section 261.33). Additionally, the disposal unit 105 can handle characteristic wastes that exhibit one or more of the four characteristics (Ignitability, Corrosively, Reactivity, and Toxicity) defined in 40 CFR Part 261, Subpart C. Any of the definitions for hazardous wastes and the requirements for handling of such found in the RCRA are to be considered within scope of the disclosure, and are able to be referenced and applied herein.

In one embodiment, wastes handled by the disposal unit 105 can include waste pharmaceuticals. Currently there are approximately 31 commercial chemical products listed on RCRA's P- and U-lists that have pharmaceutical uses. As the P- and U-lists are based on chemical designations, this number does not completely represent the total number of brand name pharmaceuticals that may actually be listed hazardous wastes. For example, the following chemotherapy drugs, CTX, Cytotoxan, Neosar and Procytox, are U058 (cyclophosamide).

In addition, waste pharmaceuticals may also be hazardous because they exhibit one or more of the four characteristics of hazardous waste: ignitability, corrosivity, reactivity and toxicity. Characteristic pharmaceutical wastes include those that exhibit the ignitability characteristic, such as solutions containing more than 24% alcohol. An example of a pharmaceutical that may exhibit the reactivity characteristic is nitroglycerine. Pharmaceuticals exhibiting the corrosivity characteristic are generally limited to compounding chemicals, including strong acids, such as glacial acetic acid, and strong bases, such as sodium hydroxide. Depending on the concentration in different pharmaceutical preparations, pharmaceuticals may also exhibit the toxicity characteristic because of the use of arsenic (D004), barium (D005), cadmium (D006), chloroform (D022), chromium (D007), lindane (D013), m-cresol (D024), mercury (D009), selenium (D010), and silver (D011). As thousands of over-the-counter or prescription drugs are currently approved for sale in the U.S., it is difficult to provide a precise number of pharmaceuticals that are listed and/or characteristic under RCRA.

The disposal unit 105 can also be adapted to handle non-hazardous wastes (e.g., waste regulated by 40 CFR Parts 239 through 259).

Additional federal regulations (not RCRA defined), such as those established by EPS, DOT, and OSHA can define rules, standards, and requirements for handling hazardous and non-hazardous wastes, which disposal unit 105 can conform to, and measurement devices 110 can assist with the compliance monitoring of.

Various state and county laws can also be utilized when defining hazardous wastes that disposal unit 105 is designed to handle in accordance with applicable regulations. For example, the Florida Administrative Code (FAC) rule chapters 62-730 define and govern hazardous wastes in Florida. Every state (and even some counties and local regulations) establish waste disposal regulations, which the disposal unit 105 and data measurement devices 110 can be adapted to handle (and to automatically monitor and report).

The reporting agencies 140 used herein can include federal, state, and local reporting agencies as well as corporate defined ones (that may not be subject to a state, federal, or local regulation.). Thus reporting agencies 140 can include, but are not limited to, the EPA, DOT, CBOX, OSHA, and state specific agencies.

Turning back to FIG. 1, the disposal unit 105 has been modified (from the cross referenced case) to contain one or more data measurements devices 110. The data measurements devices 110 can correspond to a variety of equipment designed to measure one or more relevant properties of the waste being processed by the disposal unit 105, the byproducts produced by the processing of the waste, and/or the disposal unit 105 itself. The relevant properties of waste captured by the measurement devices 110 can include those defined by federal (e.g., 40 CFR Section 260), state (e.g., FAC rules 62-730), local, or company established regulations. Thus, the disposal unit 105 and associated measurement devices 110 can be used to determine compliance with waste disposal regulation, which can occur automatically and/or with some level of manual activities being required of human agents.

For example, an electronic scale can be added to the disposal unit 105 to measure the weight of the waste being processed. Examples of other data measurements devices 110 (besides a scale) can include, but are not limited to, an air quality sensor, a manometer, a particle count sensor, a radiation sensor, an air volume sensor, and the like.

The data measurements devices 110 can communicate their readings with a data collection component 120 of a computing device 115. The computing device 115 can represent a variety of electronic components (user interfaces, etc.) configured to communicate with the disposal unit 105 and/or data measurements devices 110 and execute the commands of the data collection component 120.

In another contemplated embodiment, the computing device 115 can be implemented as an embedded computer that can be integrated within the disposal unit 105. In such an embodiment, the disposal unit 105 can be modified to include the necessary elements to allow connection to the network 160. In one embodiment, computing device 115 can be implemented modularly as a detachable component of disposal unit 105. In one embodiment, disposal unit 105 can be electronically docked to ports of a computing device 115, which permits peripheral devices (including data measurement device(s) 110), sensors, and other electronically coupled components communicate digitally encoded data. In one embodiment, the disposal unit 105 can have a docking station to perform this electronic coupling. Components of unit 105 can be communicatively linked to device 115 through wired (e.g., peripheral ports, a communication bus, etc) or wireless (e.g., BLUETOOTH, ZIGBE, WIRELESS USB, WIFI, IR, etc.) connections.

The data collection component 120 can represent a computer program product (e.g., a software/firmware application or module that is stored on a tangible storage device) configured to aggregate the waste data 135 measured by the data measurements devices 110 for a specific lot of waste being processed by the disposal unit 105. Aggregation of the waste data 135 by the data collection component 120 can also include the execution of additional operations, such as the calculation of related indices or properties, unit of measure conversions, and data formatting. The data collection component 120 can be further configured to perform basic limit checking functions, such as determining if the collected air particles require additional processing for disposal or are unsafe for unprotected handling.

Once all the waste data 135 is collected, the data collection component 120 can send the waste data 135 to the data server 125 for storage in a data store 130. The data server 125 and a data store 130 can represent the hardware and/or software components necessary to manage the electronic storage of and access to the waste data 135. For example, the data server 125 and data store 130 can be existing elements of a hospital's network 160, with a specified data section set aside for the waste data 135. Although expressed as a tangible storage medium connected to device 115 via a network 160, the disclosure is not so limited. For example, in one embodiment, store 130 can be a tangible storage medium local to device 115, such as a removal media (e.g., a removable optical media, a flash memory, etc.).

It should be appreciated that conventional methods for collecting waste data 135 are manual in nature, exposing personnel to harmful conditions when taking the measurements. Further, manual inputting of the information permits transcription errors, lost data, and other such errors that diminish an accuracy of reported information. The automated collection of waste data 135, as shown in system 100, can further reduce such exposures as well as increase measurement accuracy.

In another embodiment, system 100 can be configured to function without the network 160 component. In such an embodiment, the computing device 115 and/or data collection component 120 can be configured to provide the collected waste data 135 to an intermediary device (not shown) that can be physically transported to the data server 125 and/or data store 130. In such an embodiment, security measurements (such as use of unique identification keys per disposal unit 105, encryption techniques, metering techniques, and data tracking technologies, etc.) can be utilized to ensure data obtained from component 120 is properly and securely conveyed to server 125.

For example, the data collection component 120 can store the waste data 135 on a removable memory storage device, like a universal serial bus (USB) memory stick, which a user 155 can then disconnect from the computing device 115. The user 155 can then take the USB memory stick to the physical location of the data server 125, connect the USB memory stick to the data server 125, and transfer the waste data 135 from the USB memory stick into the data store 130.

With the waste data 135 electronically stored in a network-accessible location, the performance of tasks requiring use of the waste data 135 can be improved. Examples of such task can include, but are not limited to, report generation, data analysis, historical trend analysis, inventory management, regulatory compliance, data validation, and the like.

The additional components shown in system 100 can further illustrate this impact upon task improvement. The data server 125 can be further configured to automatically and electronically report the collected waste data 135 to a designated reporting agency 140. Such a reporting process can reduce the role of a user 155 from manually collating the waste data 135 to simply verifying the waste data 135.

Even if not automatic, a user 155 can utilize a waste management/reporting application 150 running on a client device 145 to efficiently access/process the waste data 135. The waste management/reporting application 150 can represent a software program configured to communicate with the data server 125 to access the waste data 135. The waste management/reporting application 150 can further include a variety of data analysis and/or reporting functions to allow the user 155 to perform additional operations upon the waste data 135.

For example, a user 155 can use the waste management/reporting application 150 to automatically populate an electronic form to be submitted to a reporting agency 140. In one embodiment, the reporting can also be submitted via an email message. In other embodiments, reporting can occur via an alternative electronic communication, which can be a unidirectional or bidirectional communication. For example, a cloud based collaboration space can be established for reporting, as can a network space, or a Web based one (e.g., HTTP or HTTPS compatible). Additionally, the data collection component 120, software executing on the data server 125, and/or application 150 can convert and format data collected from one or more devices 115.

For example, in one embodiment, data collected by component 120 and placed in data store 130 can be gathered and used to automatically populate an EXCEL spreadsheet (or other spreadsheet format). The spreadsheet can have columns dictated at least in part by one or more reporting agencies 140. For example, columns can include the values shown in pickup instance table 132, such as building/room, date of pickup, manifest number, a date the manifest was received, the number of days for receipt of the returned manifest form, a Boolean value (e.g., Yes/No) for whether the manifest was received within 45 days, a quantity of waste in pounds, and a set of waste codes for the waste. The EXCEL spreadsheet can be saved, manipulated, and ultimately reported to agency 140 (or data can be pulled from it to populate a form used by a reporting agency 140).

Of course, use of EXCEL is simply one example used to express an ability to adapt the data gathered herein to a set of commonly available software applications. Other software applications can be used in other contemplated embodiments of the invention. For example, a relational database management system (RDBMS) including table 132 (or attributes shown in table 132) can be used in another embodiment of the invention. Data of the data store 130 can be synchronized and/or otherwise conveyed to databases of the reporting agency 140.

Any number of optional safeguards can be implemented to ensure data accuracy and lack of manipulation occurrences. For example, in one embodiment, a data reporting agency, such as the EPA, can require data be stored in an encrypted and proprietary form, while in data store 130, which is automatically reported to agency 140. Use of an encrypted or proprietary form of data can minimize instances of tampering with the raw data. In another example, digital certificates, hidden metadata, and/or measures can be implemented to ensure the data received by the agency 140 is accurate. This represents an improvement over current practices, which are manual in nature and subject to recordation inaccuracies, transcription errors, and intentional manipulations.

In one embodiment, alerts and reporting functions can be included in system 100 to enhance safety while disposing of hazardous material. For example, one or more data measurement devices 110 can be used to sense leakages of unit 105. When a leakage is detected, an appropriate maintenance person and other appropriate personnel can be alerted via an automated text message, telephone call, fax, or other messaging technique. Further, on unit 105 alerting (such as through LED display panels, an audible warning, a problem indicating flashing light, etc.) can be implemented to ensure suitable personnel are alerted when actions related to the disposal unit 105 need to be taken. These actions can include alerts for emptying the unit 105 when full, alerts for detection of leakage that releases harmful vapors from unit 105, and the like.

Network 160 can include any hardware/software/and firmware necessary to convey data encoded within carrier waves. Data can be contained within analog or digital signals and conveyed though data or voice channels. Network 160 can include local components and data pathways necessary for communications to be exchanged among computing device components and between integrated device components and peripheral devices. Network 160 can also include network equipment, such as routers, data lines, hubs, and intermediary servers which together form a data network, such as the Internet. Network 160 can also include circuit-based communication components and mobile communication components, such as telephony switches, modems, cellular communication towers, and the like. Network 160 can include line based and/or wireless communication pathways.

As used herein, presented data store 130 can be a physical or virtual storage space configured to store digital information. Data store 130 can be physically implemented within any type of hardware including, but not limited to, a magnetic disk, an optical disk, a semiconductor memory, a digitally encoded plastic memory, a holographic memory, or any other recording medium. Data store 130 can be a stand-alone storage unit as well as a storage unit formed from a plurality of physical devices. Additionally, information can be stored within data store 130 in a variety of manners. For example, information can be stored within a database structure or can be stored within one or more files of a file storage system, where each file may or may not be indexed for information searching purposes. Further, data store 130 can utilize one or more encryption mechanisms to protect stored information from unauthorized access.

Figure 2:
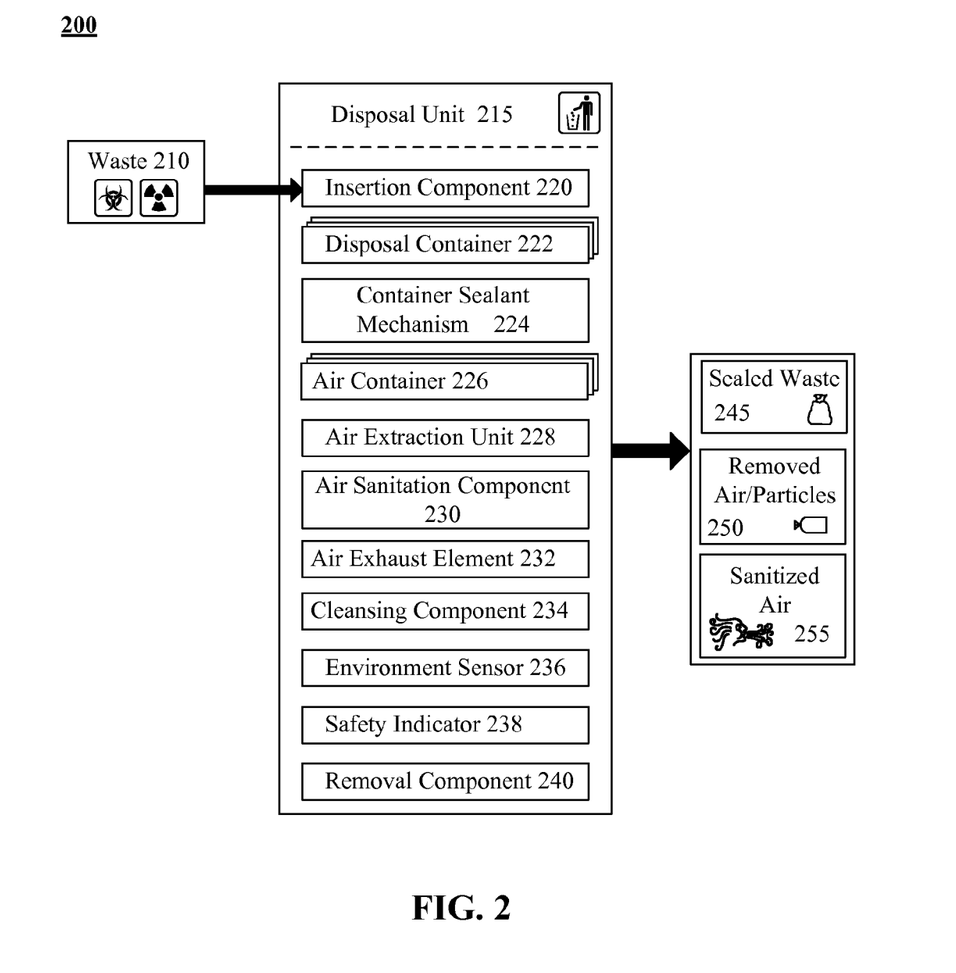
FIG. 2 is a schematic diagram of a waste disposal system 200 for safely disposing hazardous material in accordance with an embodiment of the inventive arrangements disclosed herein.

FIG. 2 is a schematic diagram of a waste disposal system 200 for safely disposing hazardous material in accordance with an embodiment of the inventive arrangements disclosed herein. As shown, waste 210 can be placed within a disposal unit 215 through an insertion component 220.

The disposal unit 215 can be a substantially closed system, designed to permit complete waste 210 containment. For example, when the waste 210 can include airborne particles, the unit 215 can be a closed, air-tight system designed to prevent an escape of airborne particles. The insertion component 220 can ensure the waste 210 is sealed once placed in unit 215 to prevent external leakages and exposure. Disposal unit 215 can be implemented as any of a variety of different disposal containers 222, each able to contain waste 210, which can be sealed by the container sealant mechanism 224 to prevent the waste 210 from escaping once contained. For example, the containers 222 can include bags, hardened plastic baskets, chemo bins, and the like. Waste disposed of in the containers 222 (which is prevented from escaping) can include vapors, radiation, and small particles.

The container sealant mechanism 224 can represent one or more mechanisms for sealing the disposal container 222. Contemplated examples of the container sealant mechanism 224 can include, but are not limited to, one or more manual manipulators, an automated vacuum-sealing component, an automated heat-sealing component, use of an adhesive to seal container 222, and the like. The seal established by the container sealant mechanism 224 can be an air tight one.

Once the disposal container 222 is sealed, an air extraction unit 228 can remove airborne particles or other potentially dangerous trace elements from the disposal unit 215. The removed air can be placed within an air container 226. In one embodiment, the air container 226 can be a separate container from disposal container 222. In another implementation, the disposal container 222 can be an air tight container that also functions as the air container 226. In still another implementation, the air container 226 can be a separately sealed container included inside the disposal container 222. Of course, using the disposal container 222 to contain air can alter an order in which the disposal container 222 is sealed relative to when the disposal unit 215 extracts the air.

After air collection and the sealing of the disposal container 222, the air collected in the air container 226 can be treated by an air sanitation component 230. The air sanitation component 230 can include one or more air treatment mechanisms configured to improve the air quality of the collected air to a predetermined/acceptable level.

Examples of air treatment mechanisms that can be utilized in the air sanitation component 230 can include, but are not limited to, a heat sterilization mechanism, an incineration mechanism, an ultraviolet (UV) disinfection mechanism, a filtration mechanism, a photo-catalytic sanitation mechanism, an oxidation mechanism, an ionization mechanism, and the like. For example, the air within the air container 226 can be exposed to a UV disinfection wand before passing through an active carbon filter. Any number (0 . . . N) of different sanitation components 230 can be cooperatively utilized.

Embodiments are contemplated, where air treatment resulting from use of one or more components 230 is sufficient to permit sanitized air to be conveyed from disposal unit 215 to an external environment, as opposed to requiring it be stored in air container 226. Further, embodiments are contemplated where sensors are used to examine air inside the unit 215, where different steps are taken based upon sensor results. For example, results can indicate that interior air of unit 215 should be cycled (0. . . N times) through one or more of the sanitation components and then ejected into an exterior environment (by air extraction unit 228). Different results can indicate that interior air of unit 215 should be captured in air container 226, then further sanitation actions (using components 230 and/or cleaning component(s) 234) should be taken to additionally cleanse unit 215 of harmful vapors/residue.

Once the collected air has been sanitized to the predetermined level, an air exhaust element 232 can be used to expel the sanitized air 255 from the disposal unit 215. The air exhaust element 232 can be configured to optionally expel the sanitized air 255 into the immediate environment of the disposal unit 215. Alternately, the air exhaust element 232 can be connected to a ventilation system (not shown) external to the disposal unit 215.

The disposal unit 215 can optionally include an additional cleansing component 234, such as a component that sprays a sanitizing liquid into the interior of disposal unit 215 to ensure the disposal unit 215 is free of waste 210. Disposal unit 215 can also include one or more optional environment sensors 236 designed to detect when the disposal unit 215 is free from harmful waste 210 (which includes vapors). The environment sensor 236 can be linked to a removal component 240 so that the removal component 240 is unable to be opened until the interior environment of the disposal unit 215 is safe.

An optional safety indicator 238 can provide an indicator as to conditions determined by the one or more environment sensors 236. For example, the safety indicator 238 can display text concerning radiation levels, airborne pathogen levels, and other important metrics concerning the interior condition of the disposal unit 215. In another example, the safety indicator 238 can be implemented as a light providing a warning when it is safe/unsafe to open the disposal unit 215. The removal component 240 can be a component through which the sealed waste 245 and/or removed air/particles 250 are able to be safely removed.

Figure 3:
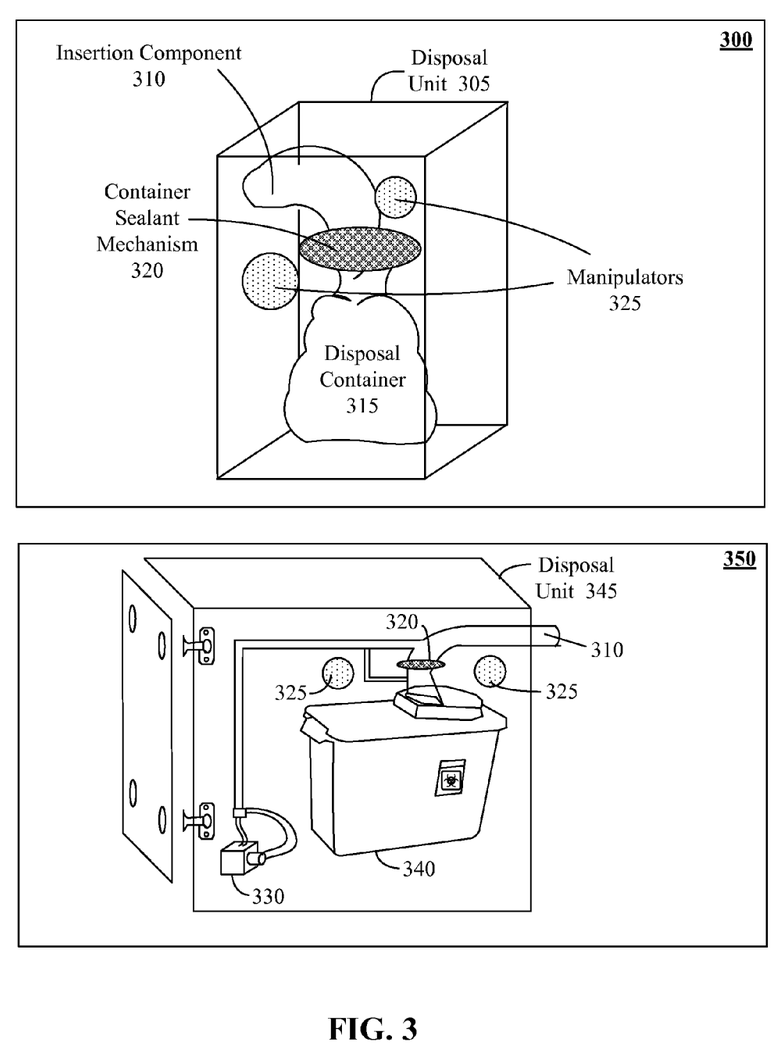
FIG. 3 is a schematic diagram of a specific implementation instance of a disposal unit that emphasizes the incorporation of a container sealant mechanism.

FIG. 3 shows a schematic diagram of a specific implementation instance 300, 350 of a disposal unit 305 that has the incorporation of a container sealant mechanism 320. Implementation instance 300, 350 can be utilized within the context of systems 100 and 200, and/or the embodiments of the disposal unit 305, 345 described within U.S. patent application Ser. No. 11/946,283. The disposal unit 305 of implementation instance 300 can be configured to utilize a container sealant mechanism 320 in addition to manipulators 325.

It is important to emphasis that in implementation instance 300, the container sealant mechanism 320 is used to seal the disposal container 315, not the manipulators 325. That is, an operator of the disposal unit 305 is not required to seal the disposal container 315 using the manipulators 325 (i.e., the operator need not use the manipulators 325 to apply a twist tie to a plastic bag 315).

The insertion component 310 for receiving waste can be terminally connected to the container sealant mechanism 320, which can be connected to the disposal container 315, such as a sealable plastic bag. The manipulators 325 can be used to connect the disposal container 315 to the container sealant mechanism 320 and/or operate the container sealant mechanism 320. Alternately, the container sealant mechanism 320 can be configured to execute automatically, triggered by the disposal unit 305. Any number of configurable conditions can trigger the automatic execution of sealant mechanism 320, such as the weight of the disposal container 315, an expiration of a maximum time that hazardous material has been left in container 315, a sensor reading indicating that a previously defined toxicity level has been reached, and other such conditions or combinations thereof A variety of container sealant mechanisms 320 can be contemplated for this implementation instance 300. In one such contemplation, the container sealant mechanism 320 can include the components to vacuum seal the disposal container 315. In another embodiment, the container sealant mechanism 320 can include parallel heating elements that collapse and melt the opening of the disposal container 315. In one embodiment, a top potion of container 315 can have a self-sealing strip, which seals the container 315 when pressed to an opposing potion of container 315 by mechanism 320. In one embodiment, an adhesive can be ejected by mechanism 320, which seals container 315.

It should be noted that the contemplated container sealant mechanisms 320 for implementation instance 300 are discussed in regards to the use of a plastic bag as the disposal container 315. However, these contemplations can be expanded to accommodate other types of disposal containers 315.

Embodiment 350 shows one such example where container 340 is incorporated within the disposal unit 345. Container 340 can be a standardized container, such as an FDA approved biohazard collection box, a sharps box for needle disposal, and the like. These types of containers are often present in doctor's offices and hospitals. These standard containers 340 are typically environmentally exposed, which causes air from the containers 340 to disseminate into the local environment. In many instances, this can result in bystanders/patients/doctors/nurses being exposed to harmful vapors, particles, and other substances. In embodiment 350, an insertion component 310 is attached to the container 340, which itself is sealed. Air can be extracted from the container, using a pump 330, where it can be optionally filtered, incinerated, or contained. Unit 345 inhibits outgoing air from container 340 from being disseminated into the local environment (one external to unit 345). When container 340 is full, manipulators 325 can be used to seal the container 340 for extraction. Alternatively, container sealant mechanism 320 can be used to seal container 340 for disposal. Container 340 can then be safely removed from unit 345 and handled properly. Components of embodiment 350 are illustrative only, and can include any of the variations of components described herein and/or described in U.S. patent application Ser. No. 11/946,283. It should be appreciated adapting unit 345 to work with existing containers 340 can minimize inventory, implementation cost, established contracts, and can ensure current disposal processes are minimally affected, while nevertheless realizing positive environmental benefits described herein.

Figure 4:
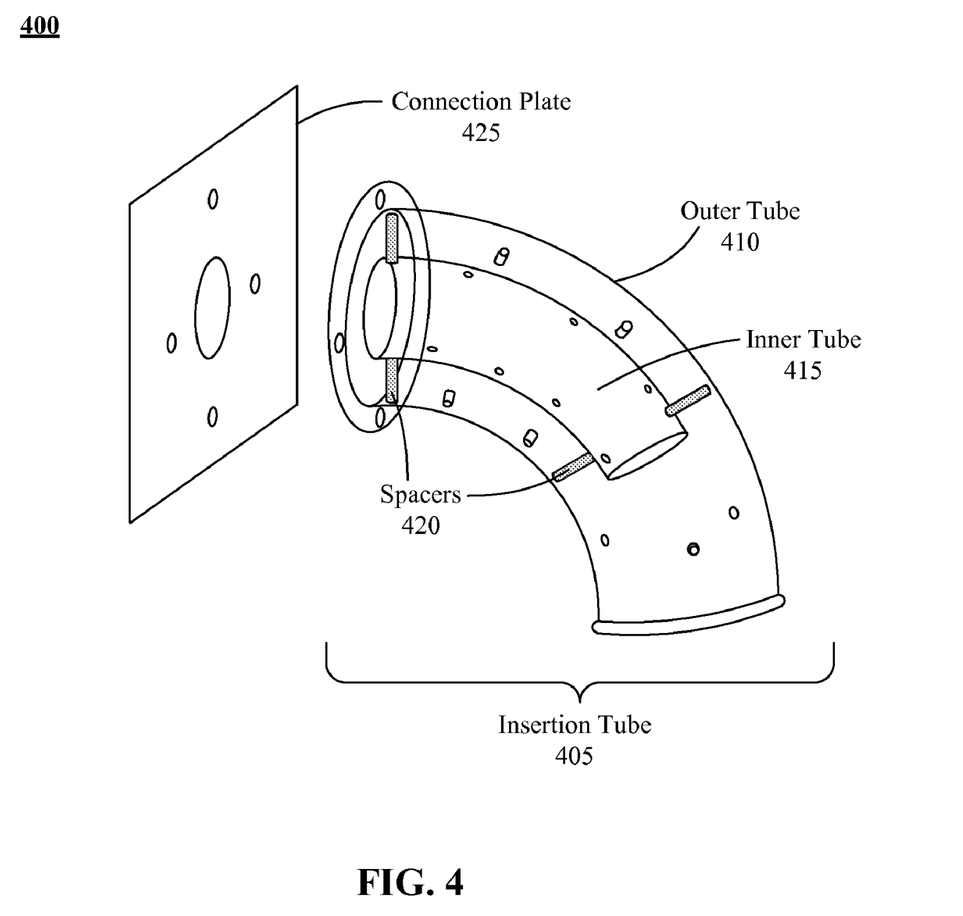
FIG. 4 illustrates a specific implementation instance of an insertion tube for the disposal unit.

FIG. 4 illustrates a specific implementation instance 400 of an insertion tube 405 for the disposal unit. Implementation instance 400 can be utilized within the context of systems 100 and 200, implementation instance 300, and/or the embodiments of the disposal unit described within U.S. patent application Ser. No. 11/946,283.

In implementation instance 400, the insertion tube 405 can be connected to a connection plate 425 within the interior of the disposal unit. The insertion tube 405 can be comprised of an outer tube 410 and an inner tube 415 that can be separated by spacers 420. Thus, both the outer tube 410 and inner tube 415 can be adjusted simultaneously by the same movement.

It should be appreciated that the insertion tube 405 shown in implementation instance 400 can allow for a variety of configurations that can be used to tailor and/or enhance the performance of the disposal unit. The following are examples highlighting these enhancement capabilities.

The outer tube 410 can be made from a material having qualities that are different and/or specific from the material that the inner tube 415 is made from. Such a configuration can be useful when the disposal unit is required to handle waste containing radioactive byproducts or ferrous metals. For example, an inner tube 415 made of a material that is magnetically inert can better ensure that ferrous metal waste does not aggregate in the insertion tube 405.

Additionally, varied configurations of materials comprising the inner tube 415 and the outer tube 410 can expand the range of waste that the disposal unit is able to process. That is, an insertion tube 405 configuration can be switched to a different configuration in order to handle a different type of waste and/or waste byproducts.

Another advantage of a dual-tube insertion tube 405 can be part longevity. For example, the insertion tube 405 can continue to function despite the presence of a defect (i.e., tear, hole, etc.) in either the inner tube 415 or the outer tube 410. That is, the outer tube 410 can be thought of as a redundant inner tube 415, allowing the disposal unit to continue functioning as long as the integrity of both tubes 410 and 415 has not been compromised.

The spacers 420 separating the inner 415 and outer tubes 410 can also be of various materials, allowing another level of insertion tube 405 customization. For example, the spacers 420 can be of a flexible material to allow for the insertion tube 405 to be moved without stressing the spacers' 420 connection points with the outer tube 410 and/or inner tube 415. This can be especially useful should the interior chamber of the disposal unit be put under the effect of a vacuum. Additionally, the quantity of spacers 420 used can be varied to handle more or less stress. In one embodiment, inhibitors can be inserted into the inner tube 415 (and/or the outer tube 415) to ensure a unidirectional flow of material (e.g., prevent backflow).

It should be noted that the configurations discussed above and presented in implementation instance 400 focus on the use of two tubes. An embodiment of the present invention is not limited as such, and can be expanded to apply to an insertion tube 405 comprising of more than two tubes. As such, the various layers of tubes can be configured to further act as a filtration mechanism for the disposal unit.

The present invention may be realized in hardware, software or a combination of hardware and software. The present invention may be realized in a centralized fashion in one computer system or in a distributed fashion where different elements are spread across several interconnected computer systems. Any kind of computer system or other apparatus adapted for carrying out methods described herein is suited. A typical combination of hardware and software may be a general purpose computer system with a computer program that, when being loaded and executed, controls the computer system such that it carries out the methods described herein.

The present invention also may be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

What is claimed is:

1. A system that collects data regarding waste processed by a disposal unit comprising:
   a disposal unit comprising:
      a substantially air tight chamber;
      an insertion component for inserting waste into the chamber;
      a substantially air tight region of the substantially air tight chamber containing a disposal container within which waste received via the insertion component is able to be placed;
      an air holding region distinct from the substantially air tight region and a remaining region of the substantially air tight chamber;
      an air extraction unit configured to capture air from the remaining region and to place the captured air in the air holding region, wherein a unidirectional air flow exists between the air holding region, and the substantially air tight region;
      a container sealant mechanism configured to seal an opening of the disposal container; and
      at least one data measurement device configured to determine at least one element of waste data, wherein said at least one element of waste data corresponds to a measurement of a property of the inserted waste;
   a data collection component configured to receive at least one element of waste data from the disposal unit; and
   a data server having a data store configured to receive and centrally store the collected waste data from the data collection component in a standardized format.

2. The system of claim 1, wherein the data collection component is an integrated component of the disposal unit.

3. The system of claim 1, wherein the collected waste data is conveyed to the data server utilizing a computer network connection, an auxiliary computing device physically transported from the data collection component to the data server, a removable storage medium physically transported from the data collection component to the data server, or combinations thereof.

4. The system of claim 1, wherein the disposal unit further comprises:
   an air sanitation component configured to sanitize the captured air to a predetermined air quality level, wherein harmful airborne byproducts of the inserted waste are of a reduced nature or neutralized.

5. The system of claim 1, wherein at least one measurement device comprises at least one of a scale for measuring a weight of the inserted waste, an air quality sensor, a manometer, a particle count sensor, a radiation sensor, and an air volume sensor.

6. The system of claim 1, further comprising:

a waste management software application configured to utilize the collected waste data to perform a plurality of data management operations, wherein said plurality of data management operations comprises at least one of a data presentation operation, a data synthesis operation, a data validation operation, a report generation operation, an operation for automatically populating data fields in a preset electronic form, and an operation for automatically conveying the collected waste data to a designated reporting agency.

7. The system of claim 1, wherein the insertion component comprises an insertion tube having a unidirectional flow mechanism, and wherein said insertion tube comprises an inner tube and an outer tube, wherein a plurality of spacers separate the outer tube from the inner tube.

8. The system of claim 1, wherein the container sealant mechanism comprises an automated heat-sealing component.

* * * * *